United States Patent [19]

Mendy

[11] 4,407,821

[45] Oct. 4, 1983

[54] LIPIDIC COMPOSITIONS FOR USE IN DIETETICS, REANIMATION AND THERAPEUTICS

[75] Inventor: Francois Mendy, Boulogne, France

[73] Assignee: Roussel UCLAF, Romainville, France

[21] Appl. No.: 302,624

[22] Filed: Sep. 15, 1981

[30] Foreign Application Priority Data

Sep. 24, 1980 [FR] France .............................. 80 20477

[51] Int. Cl.³ ...................... A61K 31/23; A61K 31/20
[52] U.S. Cl. ...................................... 424/312; 424/318
[58] Field of Search ................................ 424/312, 318

[56] References Cited

U.S. PATENT DOCUMENTS 3,993,775 11/1976 Williams .............................. 424/312

FOREIGN PATENT DOCUMENTS 2749492 5/1978 Fed. Rep. of Germany .
2197605 3/1974 France .
1446431 8/1976 United Kingdom ................ 424/318

Primary Examiner—Richard A. Schwartz
Attorney, Agent, or Firm—Bacon & Thomas

[57] ABSTRACT

Lipidic compositions for use in dietetics, reanimation and therapeutics which contain:

(A) an oil containing natural γ-linolenic acid, possibly enriched in γ-linolenic acid; or γ-linolenic acid itself or an ester thereof and (B) pure medium chain triglycerides.

25 Claims, No Drawings

LIPIDIC COMPOSITIONS FOR USE IN DIETETICS, REANIMATION AND THERAPEUTICS

The present application concerns certain new lipidic compositions usable in dietetics, reanimation and therapeutics.

Numerous pathological situations in man require substantial supply of lipids as nutritional complements or therapeutical agents. This is in particular the case in disorders of energy metabolism (during reanimation and in states of undernutrition, for example) and in disorders of lipid digestion or in metabolic diseases, such as diabetes.

The compositions which are the object of the invention are intended to be used in dietetics and in therapy in this type of situations.

The object of the present application thus consists of lipidic compositions, characterized in that they contain as principal components:

(A) an oil containing natural γ-linolenic acid, possibly enriched in γ-linolenic acid; or γ-linolenic acid itself or an ester of said acid.

(B) medium chain triglycerides, i.e. glycerol esters of fatty acids containing 6 to 12 carbon atoms.

γ-linolenic acid of the formula:

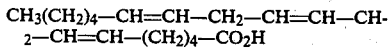

CH$_3$(CH$_2$)$_4$—CH=CH—CH$_2$—CH=CH—CH$_2$—CH=CH—(CH$_2$)$_4$—CO$_2$H is an essential fatty acid, its biological function has been described particularly by H. SPRECHER-CHUI LONGLEE BBA 1975, 398, p. 113 and H. SPRECHER, J. BENERT BBA 1975, 398, p. 353.

γ-linolenic acid is not present in any of the oils presently used in nutrition.

An easily accessible source of γ-linolenic acid usable in the composition of the invention is the oil of the seeds of plants containing γ-linolenic acid (present in the form of triglycerides) in the natural state: γ-*OENOTHERA BIENNIS* and *OENOTHERA LAMARCK IANA*-commonly called "tree primrose" or "primrose".

Among the oils containing γ-linolenic acid usable in the composition of the invention there may be cited further the oil obtained by means of the extraction of siphomycetes fungi, spirulines, maple seeds, hops. It should be understood that any other natural source of γ-linolenic acid may be used.

According to the invention, an oil containing γ-linolenic acid and enriched in γ-linolenic may also be used. The γ-linolenic acid present in such an oil enriched with the acid may be present in the acid form or in a form esterized with glycerol.

There may be used further in the compositions according to the invention in place of an oil containing γ-linolenic acid or enriched in said acid, γ-linolenic acid itself, or an ester of said acid. The ester of γ-linolenic acid used preferably is an ester of glycerol. In may also consist of an alkyl ester, such as methyl ester or ethyl ester, for example.

Medium chain triglycerides, i.e. the glycerol esters of fatty acids containing 6 to 12 carbon atoms are present in certain oils presently used in nutrition or in dietetics, but in rather low proportions. Only coconut oil contains large amounts, approximately 50%.

Certain oils do not contain any at all, such as sunflower oil.

According to the invention, in the above described compositions medium chain triglycerides present in the form of pure medium chain triglycerides are used and not in the form of an oil containing such triglycerides in a mixture with other triglycerides.

The triglycerides with medium chains may be prepared, for example, from coconut oil.

The oils containing γ-linolenic acid naturally (in the form of triglycerides) also contain other saturated or unsaturated fatty acids (again in the form of triglycerides).

Thus, the oil of OENOTHERA BIENNIS consists 80% of the following essential fatty acids:

| | |
|---|---|
| palmitic acid | 6.6% |
| palmitoleic acid | 0.1% |
| stearic acid | 1.7% |
| oleic acid (and the isomer) | 10.9% |
| linoleic acid | 71.5% |
| γ-linolenic acid | 8.6% |
| α-linolenic acid | 0.2% |
| arachidic acid | 0.3% |
| gadoleic acid | 0.1% |

The oil of OENOTHERA BIENNIS further contains 2 to 3% of an unsaponifiable fraction consisting of sterols and tocopherols.

Essential fatty acids have double functions: structural and functional.

In particular, polyunsaturated fatty acids constitute an important structural material of all of the cellular membranes:

of those of the cellules of the villi of the jejunum and of all of the particularly fragile intestinal mucous membrane impaired by lack of nutrition, of those of all other rapidly renewed tissues susceptible to being particularly affected by denutrition (macrophages, lymphocytes, platelets, red corpuscles, etc. . . . ).

The essential fatty acids also have a functional role:

they are the precursors of linear hydroxyl compounds with 20 carbon atoms, the mediators of immune processes, such as the leukotrienes, they are the precursors of prostaglandins. Linoleic acid produces two families of prostaglandins, PG$_1$ and PG$_2$.

Numerous authors emphasize the importance of linoleic acid in arterial hypertension, thrombosis, diabetes. (VERGROESEN, A. J., "Physiological effects of dietary linoleic acid", Nutr. Rev. 35, No. 1, 1977, pp. 1–5; VERGROESEN, A. J. & AL, "New aspects of the prevention of atherosclerosis by dietetics", Cah. Nutr. Diet. Vol. 14, No. 4, 1980, pp. 293–304; VLES, R. O., "Recent knowledge concerning the physiological effects of margarines high in linoleic acid", "Revue francaises des corps gras", Vol. 27, No. 3, 1980, pp. 115–120).

However, there exists a key stage in the conversion of linoleic acid to γ-linolenic acid by way of prostaglandin biosynthesis, i.e. the desaturation in position 6.

It is a limiting stage, controlled by different factors: insulin, proteins are activating factors, glucides, α-linolenic acid, fasting, age, glucagon, adrenalin, hydrocortisone, are inhibiting factors.

The importance of being able to provide γ-linolenic acid directly to the body may thus be seen.

The medium chain triglycerides representing the second essential component of the compositions that are the object of the invention, are readily assimilated by the body, even in the case where the digestion is impeded. They are much more readily assimilated than the long chain triglycerides, i.e. the glycerol esters of fatty acids containing more than 12 carbon atoms, which are the major components of numerous oils and in particular of the oils containing γ-linolenic acid naturally, such as the oil of OENOTHERA BIENNIS, the fatty acid composition of which has been given hereinabove.

Medium chain triglycerides are thus assimilable by the body even in cases wherein the digestion is impeded:

in case of defective intraluminal lipolysis due to the insufficiency or absence of pancreatic secretion, the intraluminal enzymatic hydrolysis of medium chain triglycerides is more rapid than that of long chain triglycerides. Under experimental conditions, pancreatic lipase hydrolyzes in 15 minutes more than 90% of $C_8$ triglycerides compared with 40% of the $C_{16}$ triglycerides.

in case of absorption disorders due to the insufficiency or absence of biliary salts:

biliary salts are necessary for the "solubilization" in the form of micelles of long chain triglycerides; they are not absolutely necessary for the solubilization of medium chain triglycerides and thus for their absorption;

due to insufficiency of the absorption surface of the small intestine, $C_8$ triglycerides are capable of entering directly, in contrast to those with $C_{16}$, the intestinal cells and being hydrolyzed by a cellular lipase, the absorption of medium chain triglycerides may take place to the level of the colon, while that of long chain triglycerides is terminated at the end of the jejunum (GALABERT & AL., Ann. Pediat. 1975, 22, No. 10, pp. 745–753).

It has now been discovered that it is particularly advantageous to combine the two types of the above mentioned components, the oil containing γ-linolenic acid naturally, possibly enriched in γ-linolenic acid, or the acid itself, and the medium chain triglycerides, for the reasons set forth hereinbelow.

During the conversion in the body of linoleic acid into its two higher derivatives, γ-linolenic acid and arachidonic acid, two difficulties are encountered:

(1) The desaturation of linoleic acid into γ-linolenic acid, a stage recognized as limiting. Limiting initially, this stage is rendered even more inoperative, as indicated hereinabove, by age, stress, protein deficiency, insulin insufficiency, hyperglucagonemia, all of these elements being part of the usual symptoms of severe malnutrions and of diabetes. The provision of γ-linolenic acid for the body remedies this difficulty.

(2) The second difficulty is elongation. This problem appears only in specific situations:

malnutrition, insufficient availability on the hepatic level of acetate ions usable for synthetic activity (under these conditions, an elongation activity of polyunsaturated fatty acids. The source of these acetate ions is normally the synthesis by means of the KREBS cycle from glucides, or the β-oxidation of long chain fatty acids.) During the numerous syndromes of malnutrition:

(a) the absorption of saturated, long chain fatty acids is greatly reduced, (b) in a situation of insufficient caloric input of these patients, the small amount of palmitic acid, for example, passing the intestinal barrier may be consumed during its passage, (c) the situation of the caloric deficiency of these patients, results in the fact that the few glucides available, provided by nutrition or by protidic neoglucogenesis is used first for energy needs.

In contrast, the absorption of medium chain triglycerides is not limited. The medium chain triglycerides arrive directly in the liver through the portal system and are immediately transformed into acetate links available to elongate the linoleic acid into its higher derivatives and are providing both quantities sufficient to satisfy energy needs and the amounts required to elongate the higher fatty acids.

It is therefore of particular importance to add to the oils containing γ-linolenic acid or to the acid itself, substantial amounts of medium chain triglycerides, and to supply them in the form of pure medium chain triglycerides and not in the form of other oils.

The present invention also has a special object, lipidic compositions which contain at least 50 weight percent of the medium chain triglycerides.

It is therefore more specifically the object of the present invention to provide lipidic compositions such as those defined hereinabove, wherein the ratio of the medium chain triglycerides to the γ-linolenic acid is between 10 and 100.

The preparation of the components of the compositions of the invention may be effected by methods known in the chemistry of fatty matters.

The processes mentioned hereinbelow are exemplary in nature. Such processes are known to those skilled in the art for the preparation of the components of the composition of the invention or of components with similar structures.

An oil containing naturally γ-linolenic acid may be obtained by the extraction of seeds by conventional methods, such as grinding or pressing, followed by solvent extraction.

The preparation of an oil containing naturally γ-linolenic acid and enriched in γ-linolenic acid may be effected by any selective enriching method. It is possible, for example, to effect a chemical or enzymatic hydrolysis of the triglycerides contained in the oil, separate the fatty acids obtained and to resynthesize the enriched triglycerides solely into γ-linolenic acid.

An oil enriched in γ-linolenic acid is then obtained in the form of triglycerides.

The γ-linolenic acid in the form of triglycerides may be obtained by the latter method by means of successive selective enrichments.

The preparation of an oil enriched in γ-linolenic acid may also be effected by one of the methods described in "Progress of the Chemistry of Fats and Other Lipids", Vol. 9 (1968), pp. 409–432. Among these methods, crystallization with urea may be used (reference cited on bottom of Page 423).

In this case, an oil enriched in γ-linolenic acid in the acid form is obtained (which may be esterified, if desired, by conventional methods).

By this method of crystallization with urea and by means of successive crystallizations, pure γ-linolenic acid may be obtained (it may be esterified, if so desired).

The medium chain triglycerides may be prepared from coconut oil according to the method described in "Medium Chain Triglycerides", J. R. SENIOR, editor, Philadelphia, Page 4.

The present application also has as its object lipidic compositions such as those defined hereinabove, characterized in that they also contain a liposoluble derivative of vitamin B₂.

Vitamin B₂ or riboflavin effects the activation of numerous cellular enzymes, which participate in the metabolism of carbohydrates and lipids. For this reason, Vitamin B₂ has been used as a medication in atherosclerosis. As far as is known to the present applicant, the vitamin has never been combined with lipidic compositions.

Vitamin B₂, being a factor in the utilization by the body of polyunsaturated fatty acids, is indispensable in:
oxidative metabolism,
the desaturation of fatty acids; it is particularly important to provide the body, complementing the lipidic components described, with the utilization factors of these lipids, Since lipids are involved, it is appropriate to insure a supply of vitamin B₂ in the liposoluble form.

As liposoluble derivatives of vitamin B₂, in particular fatty acid tetraesters and of riboflavin may be mentioned, such as those described in French Pat. No. 1 539 372.

The object of the present invention consists therefore in particular of lipidic compositions containing a liposoluble derivative of vitamin B₂, as described hereinabove, characterized in that the liposoluble derivative of vitamin B₂ is riboflavin tetrabutyrate.

It should be understood that the compositions that are the object of the invention may contain other components, particularly vitamin components, such as vitamin A, vitamin C, vitamin B₁₂, mineral components, antioxidants, such as vitamin E.

Vitamin C may be administered advantageously in the liposoluble form, namely in the form ascorbyl palmitate. Likewise, vitamin B₁₂ can be administred avantageously in liposoluble form example in the form of methyl cobalamine palmitate or dibencozyl palmitate. These compounds are particularly important in all methyl transfer reactions.

The object of the present invention thus consists, for example, of a lipidic composition, characterized in that it has the following approximate composition:

| | |
|---|---|
| OENOTHERA BIENNIS seed oil | 20 g |
| medium chain triglycerides | 80 g |
| riboflavin tetrabutyrate | 5000 U.I. |
| vitamin E | 150 mg |
| vitamin A | 6000 U.I. |

The compositions of the invention are thus usable in dietetics, reanimation and therapeutics.

The object of the invention also includes the application of compositions as defined hereinabove as nutriments or nutritional supplements satisfying specific nutritional needs.

Firstly, the compositions of the invention may be used in energy supply problems, when a rapidly metabolizable source of energy is required in the course of difficult operating sequences, in reanimation and in states of denutrition (needs possibly enhanced by a malabsorption phase).

Secondly, the compositions of the invention may be used in all of the situations wherein the energy balance is endangered by a disorder of lipid digestion.

This occurs in afflictions characterized by a decrease in pancreatic lipase, pancreatic insufficiencies, mucoviscidosis, absorption disorders due to a reduction in the surface if the small intestine, extended intestinal resection, fistules, celiac disorders, sprue, severe terminal ileitis, running diarrhea or a reduction in biliary salts:
intra- or extrahepatic obstruction of biliary ducts,
chronic disease of the hepatic parenchyma (hepatitis),
disturbance of the enterohepatic cycle of the bilary salts following an ileal resection.

This is also true in the case of afflictions characterized by defective metabolism on the enterocyte level: the celiac disease, surrenal insufficiency, hypobetalipoproteinemia, sprue, abetalipoproteinemia or due to an obstruction of the lymphatic ducts of malformative origin (intestinal lymphangiectasies), of infectious origin (terminal ileitis, Whipple's disease, tuberculosis), of inflammatory, traumatic, parasite or tumoral origin (lymphoma, chylous ascites or chylothorax).

A further object of the invention consists of therapeutical nutritional products containing the compositions such as those defined hereinabove, possibly in combination with a neutral carrier suitable for oral, enteral or intravenous administration.

Another object of the application is the application as medications of the compositions such as those defined hereinabove. The new compositions of the invention constitute, by virtue of their properties, highly useful medications in the treatment of the afflictions described hereinabove. They may be used furthermore, for example, in cases wherein a poor transformation of linoleic acid into its higher derivatives is observed, for example in atherosclerosis or senescence, particularly cerebral senescence, diabetes.

The usual doses of the compositions of the invention, vary (depending on the subject being treated and the case of the affliction) from 0.8 to 2 g per kilo body weight per day. When the compositions of the invention are used for purposes of therapeutic nutrition, they may be included in the quantity of lipids provided for daily consumption.

In a preferred manner, it is possible for example, to administer a dose of the compositions of the invention insuring a supply of γ-linolenic acid, by itself or in an oil containing the acid, in doses of 0.5 to 5 g, a supply of medium chain triglycerides in doses of 45 to 100 g and a supply of riboflavin tetrabutyrate in doses of 50 to 300 mg, these doses being intended per day and per oral administration for an adult.

Finally, a further object of the invention consists of pharmaceutical compositions containing a medicament as defined hereinabove, possibly in a combination with a conventional neutral carrier for oral, enteral or intravenous administration.

These pharmaceutical compositions may be present in the forms currently used in human medicine, such as for example, bottles, cans (the composition may be an oil, a lipidic emulsion), capsules or gelules.

The examples given hereinafter illustrate the invention without limiting it.

EXAMPLE 1

A dietetic composition for oral use and with the following formula, is prepared:

| | |
|---|---|
| OENOTHERA BIENNIS oil* | 20 g |
| T.C.M. (medium chain triglycerides) | 80 g |
| riboflavin tetrabutyrate | 5000 UI |
| vitamin E | 150 mg |

-continued

| | |
|---|---|
| vitamin A | 5000 UI |

The preparation of 100 kg of the above composition (100 kg) subsequently distributed into bottles or cans) is effected as follows:
(a) Formula for 100 kg:

| | |
|---|---|
| oily solution of vitamin A palmitate 1 million UI/g qsp 5000 Ui per 100 g | 5000 g |
| riboflavin tetrabutyrate qsp 1.75 mg | 1.750 g |
| dl α-tocopherol acetate qsp 150 mg | 150 g |
| Primrose oil | 20 kg |
| T.C.M. (medium chain triglycerides) qsp | 100 kg |

(b) Preparation
(1) Preparation of a concentrated solution of riboflavin tetrabutyrate Operating under nitrogen and with maximum protection against light, 2.625 g riboflavin tetrabutyrate are solubilized under agitation and at a temperature of approximately 85° C. in 2 kg medium chain triglycerides.

(2) Into a stainless steel vessel, there are introduced successively and under agitation and nitrogen:

| | |
|---|---|
| primrose oil | 20 kg |
| oily solution of vitamin A palmitate, 1 million UI/g | 5 g |
| dl α-tocopherol acetate | 150 g |
| concentrated solution of riboflavin tetrabutyrate in T.C.M. (medium chain triglycerides) | 100 kg |

EXAMPLE 2

A dietetic composition for oral use is prepared with the following formula:

| | |
|---|---|
| OENOTHERA BIENNIS* oil | 20 g |
| T.C.M. (medium chain triglycerides) | 80 g |
| riboflavin tetrabutyrate | 5000 UI |
| vitamin E | 150 mg |
| vitamin A | 5000 UI |
| ascorbyl palmitate | 200 mg |

*oil containing approximately 8% γ-linolenic acid esterified with glycerol.

EXAMPLE 3

A dietetic composition for oral use in prepared with the following formula:

| | |
|---|---|
| OENOTHERA BIENNIS oil | 20 g |
| T.C.M. (medium chain triglycerides) | 80 g |
| riboflavin tetrabutyrate | 5000 UI |
| vitamin E | 150 mg |
| vitamin A | 5000 UI |
| dibencozyl palmitate | 150 μg |

EXAMPLE 4

Compositions for oral use distributed in bottles, containing fractionated *OENOTHERA BIENNIS* oil with approximately 40% γ-linolenic acid (esterified with glycerol) of the following formula are prepared:

| | | | |
|---|---|---|---|
| OENOTHERA BIENNIS oil enriched to 40% γ-linolenic acid | 10 g | 8 g | 6 g |
| T.C.M. (triglycerides with with medium chains | 90 g | 92 g | 94 g |
| Riboflavin tetrabutyrate | 5000 UI | 5000 UI | 5000 UI |
| Vitamin E | 150 mg | 150 mg | 150 mg |
| Vitamin A | 5000 UI | 5000 UI | 5000 UI |

The manufacturing method set forth in Example 1 is used.

EXAMPLE 5

Compositions for oral use distributed in bottles, containing fractionated *OENOTHERA BIENNIS* oil with approximately 70% γ-linolenic acid (esterified with glycerol) are prepared by the following formula:

| | | | | |
|---|---|---|---|---|
| OENOTHERA BIENNIS oil enriched to approximately 70% γ-linolenic acid | 8 g | 6 g | 4 g | 3 g |
| T.C.M. (medium chain triglycerides) | 92 g | 94 g | 96 g | 97 g |
| Riboflavin tetrabutyrate | 5000 UI | 5000 UI | 5000 UI | 5000 UI |
| Vitamin E | 150 mg | 150 mg | 150 mg | 150 mg |
| Vitamin A | 5000 UI | 5000 UI | 5000 UI | 5000 UI |

EXAMPLE 6

Compositions for oral use, distributed in bottles, containing γ-linolenic acid in the form of triglycerides, are prepared by the following formula:

| | | | | |
|---|---|---|---|---|
| γ-linolenic acid (triglycerides) | 5 g | 4 g | 3 g | 2 g |
| T.C.M. (medium chain triglycerides) | 95 g | 96 g | 97 g | 98 g |
| Riboflavin tetrabutyrate | 5000 UI | 5000 UI | 5000 UI | 5000 UI |
| Vitamin E | 150 mg | 150 mg | 150 mg | 150 mg |
| Vitamin A | 5000 UI | 5000 UI | 5000 UI | 5000 UI |
| Ascorbyl palmitate | 200 mg | 200 mg | 250 mg | 250 mg |

EXAMPLE 7

Soft capsules of the following formula are prepared:

| | |
|---|---|
| γ-linolenic acid | 100 mg |
| Medium chain triglycerides | 100 mg |
| Riboflavin tetrabutyrate | 10 UI |
| Vitamin E | 1 mg |
| Vitamin A | 10 UI |

EXAMPLE 8

Gelules of the following formula are prepared:

| | |
|---|---|
| γ-linolenic acid | 75 mg |
| medium chain triglycerides | 75 mg |
| Riboflavin tetrabutyrate | 10 UI |
| Vitamin E | 1 mg |
| Vitamin A | 10 UI |
| Aerosil | 150 mg |

EXAMPLE 9

An emulsion for intravenous use is prepared by the following formula:

|  | 100 ml = 1 bottle | 5 liter = 50 bottles |
|---|---|---|
| OENOTHERA BIENNIS oil | 4 g | 200 g |
| Medium chain triglycerides | 16 g | 800 g |
| dl α-tocopherol acetate | 0.1 g | 5 g |
| Soy bean lecithin | 0.2 g | 60 g |
| N Glycerin | 1.8 g | 90 g |
| Sodium hydroxide, qsp pH = 7.3 | 0.8 ml | 40 ml |
| Distilled water | 76.9 g | 3845 g |
| (2.65% additional water are added to compensate for evaporation.) | | |

EXAMPLE 10

Emulsion for intravenous use

|  | 100 ml = 1 bottle | 5 liter = 50 bottles |
|---|---|---|
| OENOTHERA BIENNIS oil | 4 g | 200 g |
| Medium chain triglycerides | 16 g | 800 g |
| Riboflavin tetrabutyrate | 5000 UI | 250 000 UI |
| dl α-tocopherol acetate | 0.1 g | 5 g |
| Soy bean lecithin | 0.2 g | 60 g |
| N glycerin | 1.8 g | 90 g |
| Sodium hydroxide, qsp pH 7.3 | 0.8 ml | 40 ml |
| Distilled water | 76.9 g | 3845 g |
| (2.65% additional water is added to compensate for evaporation) | | |

EXAMPLE 11

Emulsion for oral use

|  | 100 ml = 1 bottle | 5 liter = 50 bottles |
|---|---|---|
| OENOTHERA BIENNIS oil | 4 g | 200 g |
| Medium chain triglycerides | 16 g | 800 g |
| dl α-tocopherol acetate | 0.1 g | 5 g |
| Soy bean lecithin | 0.2 g | 60 g |
| N glycerin | 1.8 g | 90 g |
| Sodium hydroxide qsp pH = 7.3 | 0.8 ml | 40 ml |
| Artificial sweetener | 0.5 ml | 25 ml |
| Distilled water | 76.4 g | 3820 g |
| (2.65% additional water is added to compensate for evaporation) | | |

EXAMPLE 12

Emulsion for oral use

|  | 100 ml = 1 bottle | 5 liter = 50 bottles |
|---|---|---|
| OENOTHERA BIENNIS oil | 4 g | 200 g |
| Medium chain triglycerides | 16 g | 800 g |
| Riboflavin tetrabutyrate | 5000 UI | 250 000 UI |
| dl α-tocopherol acetate | 0.1 g | 5 g |
| Soy bean lecithin | 0.2 g | 60 g |
| N glycerin | 1.8 g | 90 g |
| Sodium hydroxide qsp pH = 7.3 | 0.8 ml | 40 ml |
| Artificial sweetener | 0.5 ml | 25 ml |
| Distilled water | 76.4 g | 3820 g |
| (2.65% additional water is added to compensate for evaporation) | | |

I claim:

1. A lipidic composition for use in reanimation, dietetics and in situations wherein the energy balance is endangered by a disorder of lipid digestion comprising:
   (A) an oil naturally containing γ-linolenic acid, said oil enriched in γ-linolenic acid, or γ-linolenic acid, an ester of said acid, or mixtures thereof; and
   (B) pure medium chain triglycerides of fatty acids containing 6 to 12 carbon atoms and comprising at least 50% by weight of the composition, wherein the ratio of the medium chain triglyceride component to the γ-linolenic component is between 10 and 100.

2. A lipidic composition according to claim 1 wherein the component A is oil of ONEOTHERA BIENNIS or OENOTHERA LAMARCK IANA, natural or enriched in γ-linolenic acid.

3. A lipidic composition according to claim 1, wherein component A is γ-linolenic acid or an ester of said acid.

4. A lipidic composition according to one of claims 1 to 3, which also contains a liposoluble derivative of vitamin $B_2$.

5. A lipidic composition according to claim 4, wherein the liposoluble derivative of vitamin $B_2$ is riboflavin tetrabutyrate.

6. A lipidic composition according to one of claims 1 to 3, which also contains a liposoluble derivative of vitamin C.

7. A lipidic composition according to claim 6, wherein the liposoluble derivative of vitamin C is ascorbyl palmitate.

8. A lipidic composition according to one of claims 1 to 3 characterized in that they also contain a liposoluble derivative of $B_{12}$ which is dibencozyl palmitate or methyl cobalamine palmitate.

9. A lipidic composition according to any one of claims 1 to 3 characterized in that they have the following approximate composition:

| OENOTHERA BIENNIS seed oil | 20 g |
|---|---|
| medium chain triglycerides | 80 g |
| riboflavin tetrabutyrate | 5000 UI |
| vitamin E | 150 mg |
| vitamin A | 5000 UI |

10. A lipidic composition according to claim 1 which also contains a liposoluble derivative of vitamin $B_2$.

11. A lipidic composition according to claim 10 wherein the liposoluble derivative of vitamin $B_2$ is riboflavin tetrabutyrate.

12. A lipidic composition of claim 1 which also contains a liposoluble derivative of vitamin C.

13. A lipidic composition of claim 4 which also contains a liposoluble derivative of vitamin C.

14. A lipidic composition of claim 5 which also contains a liposoluble derivative of vitamin C.

15. A lipidic composition according to claim 1 which also contains ascorbyl palmitate.

16. A lipidic composition according to claim 12 wherein the vitamin C derivative is ascorbyl palmitate.

17. A lipidic composition according to claim 14 wherein the derivative of vitamin C is ascorbyl palmitate.

18. A composition according to claim 1 which also contains a liposoluble derivative of vitamin $B_{12}$ which is dibencozyl palmitate or methyl cobalamine palmitate.

19. A composition according to claim 4 which also contains a liposoluble derivative of vitamin $B_{12}$ which is dibencozyl palmitate or methyl cobalamine palmitate.

20. A lipidic composition of claim 6 which also contains a liposoluble derivative of vitamin $B_{12}$ which is dibencozyl palmitate or methyl cobalamine palmitate.

21. A nutritional supplement containing the composition according to any one of claims 1 to 3, in combination with a neutral carrier suitable for oral, enteral or intraveneous administration.

22. A pharmaceutical composition containing the composition of claim 1, 2 or 3, in combination with a conventional carrier suitable for oral, enteral or intraveneous administration.

23. A method of compensating for a condition wherein the energy balance is endangered by a disorder of lipid digestion which comprises administering to a patient having such a condition an effective amount of the composition of claims 1, 2 or 3 to mitigate said condition.

24. A method of reanimation which comprises the administration of the composition of claim 1 to a human being in need of reanimation.

25. A method of overcoming a disorder of lipid digestion by providing a human being in need thereof, with the composition of claim 1.

* * * * *